US008563778B2

(12) United States Patent
Hanson et al.

(10) Patent No.: US 8,563,778 B2
(45) Date of Patent: Oct. 22, 2013

(54) PROCESS TO PREPARE ETHYLENE AMINES

(75) Inventors: Martin Stefan Hanson, Göteborg (SE); Leif Kenny Christian Gustafson, Hjälteby (SE); Johan Lif, Skärhamn (SE); Boris Kuzmanovic, Utrecht (NL); Ulf Schröder, Göteborg (SE)

(73) Assignee: Akzo Nobel N.V., Arnhem (NL)

( * ) Notice: Subject to any disclaimer, the term of this patent is extended or adjusted under 35 U.S.C. 154(b) by 195 days.

(21) Appl. No.: 12/811,527

(22) PCT Filed: Dec. 29, 2008

(86) PCT No.: PCT/EP2008/068306
§ 371 (c)(1),
(2), (4) Date: Sep. 16, 2010

(87) PCT Pub. No.: WO2009/083580
PCT Pub. Date: Jul. 9, 2009

(65) Prior Publication Data
US 2011/0015439 A1     Jan. 20, 2011

Related U.S. Application Data

(60) Provisional application No. 61/022,610, filed on Jan. 22, 2008.

(30) Foreign Application Priority Data

Jan. 3, 2008   (EP) ..................... 08100075

(51) Int. Cl.
C07C 209/16   (2006.01)

(52) U.S. Cl.
USPC ........... 564/475; 564/479; 564/480; 564/497; 564/498

(58) Field of Classification Search
None
See application file for complete search history.

(56) References Cited

U.S. PATENT DOCUMENTS

| | | | |
|---|---|---|---|
| 2,365,721 A | 12/1944 | Olin et al. | |
| 2,861,995 A | 11/1958 | MacKenzie et al. | |
| 3,270,059 A | 8/1966 | Winderl et al. | |
| 4,123,462 A | 10/1978 | Best | |
| 4,404,405 A | 9/1983 | Winters | |
| 5,030,740 A | 7/1991 | Bowman et al. | |
| 6,821,396 B2 | 11/2004 | Wolfert et al. | |
| 7,034,186 B2 | 4/2006 | Gerlach et al. | |
| 7,696,384 B2 | 4/2010 | Cauwenberge et al. | |
| 2003/0089591 A1 | 5/2003 | Wolfert et al. | |
| 2007/0043217 A1 | 2/2007 | Siegert et al. | |
| 2007/0100144 A1 | 5/2007 | Frauenkron et al. | |
| 2010/0087684 A1 | 4/2010 | Do et al. | |

FOREIGN PATENT DOCUMENTS

| | | |
|---|---|---|
| DE | 217 508 A1 | 1/1985 |
| DE | 101 53 410 A1 | 5/2003 |
| EP | 0 146 508 A2 | 6/1985 |
| EP | 0 197 612 A2 | 10/1986 |
| EP | 0 729 785 A1 | 9/1996 |
| EP | 0 737 669 A1 | 10/1996 |
| GB | 1027508 | 4/1966 |
| JP | 61-280455 A | 12/1986 |
| JP | 7-323226 A | 12/1995 |
| RU | 1786021 A1 | 1/1993 |
| WO | WO 2007/036498 A1 | 4/2007 |

OTHER PUBLICATIONS

International Search Report for International Application No. PCT/EP2008/068306, Apr. 1, 2009.
European Search Report for Application No. 08100075.4, May 16, 2008.
Process Economics Program Report No. 138 Alkyl Amines, SRI International (Mar. 1981).
Fischer et al., "Amination of diols and polyols to acyclic amines," Catalysis Today 37, pp. 167-189 (1997).
Fischer et al., "Cobalt-catalyzed Amination of 1,3-Propanediol: Effects of Catalyst Promotion and Use of . . . ," Journal of Catalysis 183, pp. 373-383 (1999).
Fischer et al., "Continuous Amination of Propanediols in Supercritical Ammonia," Angew. Chemi. Int. Ed. vol. 38, No. 3, pp. 351-354 (1999).
Fisher et al., "Nickel-catalyzed amination of 1,3-propanediols differently substituted at . . . ," Journal of Molecular Catalysis A: Chemical 149, pp. 197-204 (1999).
English Abstract of DD 217 508 A1, Abstract No. 85-116505/20, Jan. 16, 1985.
English Abstract of EP 0 729 785 A1, Sep. 4, 1996.
Derwent Abstract of SU 1786021A1, Abstract No. 94-033102/04, Jan. 7, 1993.
ChemAbstract 111:221883; Abstract of Journal of Photochemistry and Photobiology, A: Chemistry, 49(1-2), 53-61 (1989).
Patent Abstracts of Japan of JP 07-323226 A (publication date Dec. 12, 1995).
English language Partial Translation of JP 07-323226 A (publication date Dec. 12, 1995).
JP Office Action for Patent Application No. 2010-541054 dated Nov. 20, 2012.
JP English language machine translation for Office Action for Patent Application No. 2010-541054 dated Nov. 20, 2012.

*Primary Examiner* — Brian J Davis
(74) *Attorney, Agent, or Firm* — Robert C. Morriss

(57) ABSTRACT

The present invention relates to a process to prepare ethylene amines by the amination of ethylene oxide, ethylene glycol or ethanolamine in the presence of a catalyst, comprising a step wherein methylamine and/or ethylamine are removed from the reaction effluents.

14 Claims, 3 Drawing Sheets

PROCESS TO PREPARE ETHYLENE AMINES

The present application claims priority of EP application No. 08100075.4 filed on Jan. 3, 2008 and U.S. provisional application No. 61/022,610 filed on Jan. 22, 2008.

The present invention relates to an improved process to prepare ethylene amines

Ethylene amines are used as solvents, stabilizers, starting materials for the synthesis of chelating agents, fungicides, micronutrients, synthetic resins, fibres, medicaments, inhibitors, and interface-active substances.

In particular, ethylene diamine (EDA) is used as a raw material for the preparation of a number of chemicals such as chelating agents, fungicides, and synthetic resins like fibres.

Ethylene amines, such as ethylene diamine and diethylene triamine, are prepared by the amination of ethylene oxide, ethylene glycol or ethanolamines in the presence of a catalyst. These reactions take place at a high pressure and a high temperature and lead to the formation of a number of side products as well.

The amination of ethylene glycol or ethylene oxide in a first step gives ethanolamines, such as monoethanol amine and diethanol amine, which in a subsequent step are aminated to give the desired ethylene amine.

Many documents disclose a process to prepare ethylene amines including all sorts of different steps to obtain the purest product reasonably possible.

For example, EP 197612 discloses a process for utilizing a reaction zone containing a catalyst to conduct amine condensation reactions and a separation zone to conduct separations of the reaction products of such reactions. The amine condensation reaction may be a reaction to prepare ethylene diamine from ammonia and monoalkanolamine or ethylene oxide and ammonia. It is said that in the production of ethylene diamine the effluent gas stream from the amination zone will be subjected to distillation to remove water, ammonia, ethylene diamine, monoethyl piperazine, hydroxyethyl piperazine, aminoethyl ethanolamine, tetraethylene pentamine, diethylene triamine, aminoethyl piperazine, piperazine, triethylene tetraamine, diethanolamine, and triethanolamine.

In the ethylene amine production process ethylamine and methylamine are formed as side products. Though applicant does not wish to be bound by any theory, it is thought that methylamine is formed via dehydrogenation of monoethanolamine to the aldehyde, followed by decarbonylation to methylamine. Ethylamine is thought to be formed via a different mechanism: either by direct hydrogenolysis of monoethanolamine or by dehydration of the monoethanolamine to the unsaturated amine followed by hydrogenation to ethylamine.

Methylamine and ethylamine are capable of further reaction with ethanolamines or ethylene amines to give several alkyl-ended ethylene amines, which are undesired and should be removed from the desired amine- and hydroxyl-terminated compounds.

In the process as specified in the Examples of EP 197 612 the above is exactly what happens, ethylamine and methylamine will be partly flashed off with the ammonia and the remaining amount will be stripped off with the ammonia. In consequence, the ethylamine and methylamine formed will be recycled back into the process until they react with one of the reactants to give a number of undesired side-products, some of which are hard to separate from the desired ethylene diamine product.

A. Fischer et al. in "Amination of Diols and Polyols to Acyclic Amines", *Catalysis Today* 37 (1997), pp. 167-189 describe a process to aminate ethylene oxide or monoethanolamine to ethylene diamine. The formation of ethylamine is suggested in a process that is zeolite catalyzed. However, nothing is said about the amount in which it is formed (if any). Also, it is not disclosed that the formation of ethylamine is undesired and that it should be removed.

In consequence, in the art the formation of ethylamine and methylamine is not acknowledged to pose a problem.

It has now been found that keeping methylamine and ethylamine in the process streams, which will inherently additionally result in a number of other ethylated and methylated side products, such as methylethylene diamine or ethylethylene diamine, methyldiethylene triamine, ethyldiethylene triamine, is undesired if the ethylene amine product is to be used as a raw material, e.g. for fungicide production or fibre production.

In the production of fungicides ethylene diamine is reacted with $CS_2$ and NaOH. If the ethylene diamine product contains methylated and ethylated side products, more COD is found in the waste water, which is highly undesirable for the environment.

In the production of fibres such as LYCRA® stretch fibres, methylated and ethylated ethylene diamines prohibit sufficient crosslinking, making the fibres less durable.

The above problems can be removed by the process of the present invention.

The present invention provides a process to prepare ethylene amines by the amination of ethylene oxide, ethylene glycol or ethanolamine in the presence of a catalyst, comprising a step wherein methylamine and/or ethylamine are removed from the reaction effluents.

By reaction effluents are meant any reaction streams that are recycled or enter into the several reaction zones as well as the reaction zones themselves.

In a preferred embodiment the excess of aminating compound is recycled for reuse in the process.

The aminating compound may be any compound suitable to aminate a hydroxyl group or a latent hydroxyl group, like an epoxide group, and in one embodiment can be selected from the group of alkylamines, alkanolamines, aromatic amines or ammonia. Preferably, the aminating compound is ammonia.

In another preferred embodiment, methylamine and/or ethylamine are removed by a distillation step, an absorption step, an adsorption step, a cracking step or a combination of two or more of such steps; preferably, the methylamine and/or ethylamine are removed by a distillation step.

For the purposes of this application, by cracking is meant heating in the presence or absence of hydrogen and/or a catalyst to result in the decomposition of the molecules into smaller ones. A cracking catalyst typically consists of supported metal sulfides or nitrides or possibly of a heterogeneous acid, such as a zeolite. The cracking process suitably proceeds at temperatures above 200° C. and at hydrogen pressures below 20 bar.

Distillation includes both classic distillation in a separate distillation column and (reactive) distillation in the reaction zone.

The ethanolamine preferably is monethanolamine or diethanolamine or a mixture of these two; most preferably, the ethanolamine is monoethanolamine.

In one embodiment it was found that methylamine and ethylamine can be suitably adsorbed onto or absorbed by absorbents and adsorbents such as on exchange resins. These adsorbents/absorbents were found to be selective for the removal of small amines present in low weight percent concentrations in ammonia. The adsorption capacity towards methylamine increases when the acidic strength of the adsorbent decreases. Also, the adsorbed methylamine and ethylamine can be desorbed from the adsorbent, and hence the adsorbent material can be used for bed regeneration. Drying of the ion exchange resin after washing with aqueous streams is not needed, at least not to maintain the adsorption capacity and selectivity. The adsorption capacity of the acidic ion exchange resin was found not to decrease after several adsorption/desorption cycles. Surprisingly, even typical physisorbents such as activated carbon or AMBERSORB® 563 adsorbent show satisfying adsorption performance for the removal of small amines from ammonia and thus can be used for the removal of methylamine and ethylamine in an ethylene amine production process. The absorption/adsorption can take place in the liquid as well as the gas phase. In one embodiment the absorption/adsorption step takes place at or just below room temperature or at an elevated temperature; preferably, the temperature is between room temperature and 50° C.

In another embodiment it was found that methylamine and ethylamine can be suitably removed by cracking them in the presence or absence of hydrogen and/or a catalyst. Typical catalysts made for cracking are metal sulfides or metal nitrides, but also pure acid catalysts such as zeolite or NAFION® sulfonated tetrafluoroethylene based fluoropolymer-copolymer-super-acid catalyst can be used. Metals often used in these catalysts are Mo, W, Ni, and Co. Cracking is done at high temperatures, generally above 180° C., preferably above 200° C., even more preferably above 215° C., and low hydrogen pressures, generally below 20 bar, preferably below 15 bar, more preferably below 10 bar. Ethylamine and methylamine are cracked to give ethane and ammonia and methane and ammonia, respectively. Ethane and methane are inert and so volatile that they can be purged out of the process.

In yet another embodiment, it was found that methylamine and ethylamine can be suitably removed by a distillation step, as they have a different boiling point from the boiling points of the other components present in the reaction streams.

In a preferred embodiment after the amination reaction, first the excess aminating compound is removed together with the methylamine and/or ethylamine and subsequently the methylamine and ethylamine are removed from the aminating compound. In this way "clean" aminating compound is acquired that can be recycled to the process and reused for a further amination.

In an alternative preferred embodiment, after the amination reaction first the main part of the excess of aminating compound is removed (to be recycled for reuse) and subsequently the rest of the excess aminating compound is removed together with the methylamine and/or ethylamine. By "main part" is meant an amount of 75 to 99% of the excess of aminating compound In a more preferred embodiment, methylamine and ethylamine are separated off by performing a distillation step in an early stage of the production process, e.g. in the step where excess $NH_3$ is stripped off.

It should be understood that the methylamine and ethylamine can of course be separated from the aminating compound in the streams containing both aminating compound and methylamine and/or ethylamine.

It was found for example that methylamine and ethylamine can be conveniently removed from the process together with ammonia and a small amount of water and subsequently be easily separated from the ammonia.

In a set-up in the distillation step, $NH_3$ is separated off as the top product and a mixture of methylamine, ethylamine, and water is separated off as the bottom product.

The advantages of the preferred early separation of methylamine and ethylamine (MA/EA) in a MA/EA distillation tower are that because the amount of side products will be significantly reduced, fewer ethylene amine purification steps are needed.

The catalyst that can be suitably used in the process of the invention may be any catalyst known to be fit for an amination reaction, for instance a catalyst containing a catalytically active compound on a solid support. Usually the catalyst contains as the catalytically active part at least one metal selected from the group consisting of nickel, chromium, cobalt, copper, ruthenium, iron, calcium, magnesium, strontium, lithium, sodium, potassium, barium, cesium, tungsten, silver, zinc, uranium, titanium, rhodium, palladium, platinum, iridium, osmium, gold, molybdenum, rhenium, cadmium, lead, rubidium, boron, and manganese, or mixtures thereof. The metallic part of the catalyst, which has the main responsibility for the dehydrogenation/hydrogenation catalytic effect, contains at least 70% by weight, preferably above 80% by weight, of nickel, chromium, cobalt, copper, palladium, ruthenium or iron or mixtures thereof. The catalytic effects are often promoted to achieve, e.g., improved selectivity for desired products, by the presence of minor amounts of other metals, such as those selected from the group consisting of calcium, magnesium, strontium, lithium, sodium, potassium, barium, cesium, tungsten, iron, ruthenium, zinc, uranium, titanium, rhodium, palladium, platinum, iridium, osmium, silver, gold, molybdenum, rhenium, cadmium, lead, rubidium, boron, and manganese. These promoters normally constitute from 0.1 to 30%, preferably from 1 to 20% by weight, of the total amount of catalytic metals. The catalytic metals are normally supported by a porous metal oxide carrier, although other types of carriers, such as carbon, may also be utilized. Examples of suitable support materials are various forms of alumina, silica, diatomaceous earths, alumina-silica, alumina-titania, alumina-magnesia, and alumina-zirconia. The carrier normally constitutes between 50 and 97% by weight of the whole catalyst. In a preferred embodiment, the catalyst is a metallic catalyst containing nickel and promoted with ruthenium, rhenium, palladium or platinum or mixtures thereof in metallic form on a porous metal oxide support containing alumina. Dehydrogenation/hydrogenation catalysts as described above can be found for example in EP-A 146 508, EP-A-729 785, EP-A-737 669, U.S. Pat. No. 2,365,721, and U.S. Pat. No. 4,123,462.

The temperature used for the amination step is generally between 120° C. and 300° C., preferably in the range between 175° C. and 225° C.

The pressure used for the amination step is generally between 8 and 40 MPa and preferably from 15 to about 30 MPa.

EXAMPLES

Example 1

Removal of Ethylamine from an Ammonia-Containing Mixture by Cracking

A 300 ml autoclave, equipped with a stirrer and temperature control was flushed with nitrogen gas. The autoclave was charged with 5 grams of NAFION® sulfonated tetrafluoroethylene based fluoropolymer-copolymer super-acid catalyst as catalyst, 31 grams of ammonia, 11 grams of ethylamine, and 800 kPa of hydrogen. The autoclave was heated to 220° C. and kept at this temperature with continuous stirring for 2 hours.

Samples were withdrawn from the autoclave after the reaction and analyzed using Gas Chromatography. The conversion of the ethylamine was calculated to be 1.5% and the product selectivity was calculated to be 41.3% ethane.

Comparative Example

Conventional Process To Prepare Ethylene Diamines
(In Accordance With EP 0 197 612)

Figure 1:
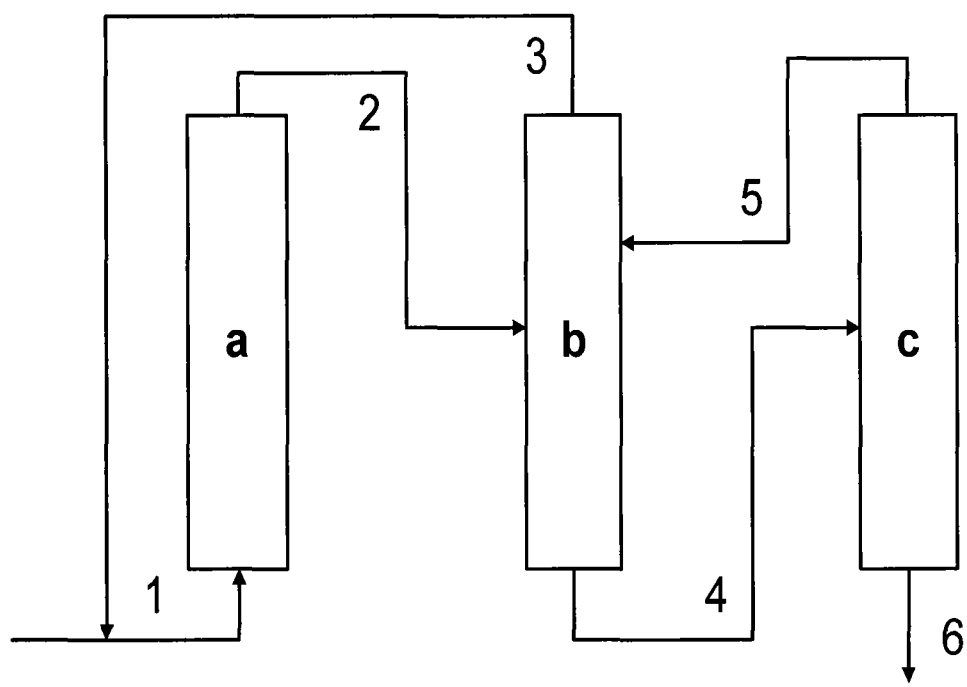
FIG. 1 shows a conventional process to prepare ethylene diamines.

FIG. 1 shows a conventional process to prepare ethylene diamines, consisting of separation of the ethylene amine synthesis mixture, after performing the reaction in unit "a". The reaction in unit "a" is carried out under normal amination conditions, as described above. The product mixture, stream 2, is distilled in column "b" at 21 bar and with a bottom temperature of 185° C. At the top of the column, stream 3, ammonia is removed together with hydrogen, methylamine, and ethylamine. Stream 3 is re-circulated back to the reactor, where methylamine and ethylamine react to form alkyl-ended ethylene amines. The bottom, stream 4, is further distilled in column "c" at 1 bar and with a bottom temperature of 130° C. The top, stream 5, from column "c" is returned to column "b" and the bottom, stream 6, consists of amines and water. Stream 6 is distilled further to separate the different amines produced. The composition of the streams can be seen in Table 1.

TABLE 1

| Stream[1] | 2 | 3 | 4 | 5 | 6 |
|---|---|---|---|---|---|
| $NH_3$ | 46.3 | 99.7 | — | — | — |
| Amines[2] | 47.0 | — | 88.4 | — | 99.1 |
| Water | 6.5 | — | 11.5 | 96.3 | 0.9 |
| Methylamine | 0.09 | 0.21 | — | — | — |
| Ethylamine | 0.11 | 0.10 | 0.1 | 3.7 | — |

[1]expressed as a percentage
[2]produced ethyleneamines

Example 2

Figure 2:
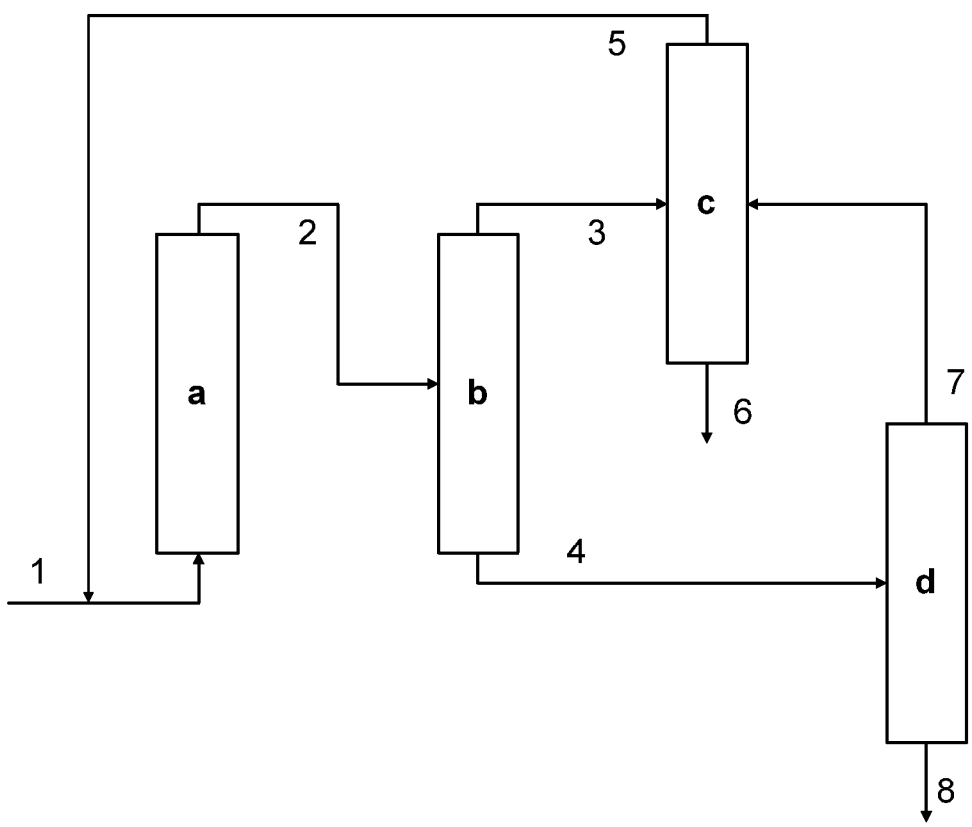
FIGS. 2 and 3 show processes to prepare ethylene diamines according to the invention, where amines are removed from the reaction effluents.

Removal of Methylamine and Ethylamine From a Product Mixture by Parallel Distillation FIG. 2 shows the separation of an ethylene amine synthesis mixture after performing the reaction in unit "a". The reaction in unit "a" is the same as in the Comparative Example. The product mixture, stream 2, is distilled in column "b" at 17 bar and with a bottom temperature of 247° C. At the top of the column, stream 3, ammonia is removed together with hydrogen, methylamine, and ethylamine. The overhead take-off stream, stream 3, is distilled in column "c" at 17 bar with a bottom temperature of 189° C. Here methylamine and ethylamine are removed by the bottom, stream 6, and the top stream, stream 5, is re-circulated back to the reactor. Stream 4 is distilled in column "d" at 1 bar and with a bottom temperature of 130° C. The top stream, stream 7, from column "d" is returned to column "c". The bottom stream, stream 8, consists of the amines and water and is distilled further to separate the different amines produced. The composition of the streams can be seen in Table 2.

TABLE 2

| Stream[1] | 2 | 3 | 4 | 5 | 6 | 7 | 8 |
|---|---|---|---|---|---|---|---|
| $NH_3$ | 46.3 | 99.7 | — | 100 | 1 | — | 0 |
| Amines[2] | 47 | — | 88.4 | — | — | — | 99.1 |
| Water | 6.5 | — | 11.5 | — | 88.5 | 96.3 | 0.9 |
| Methylamine | 0.09 | 0.22 | — | 0.01 | 4.9 | — | — |
| Ethylamine | 0.11 | 0.1 | 0.1 | — | 5.63 | 3.68 | — |

[1]expressed as a percentage
[2]produced ethyleneamines

It can be seen that the major amounts of ethylamine and methylamine leave the process mixture through stream 6 and do not end up in stream 5.

Example 3

Figure 3:
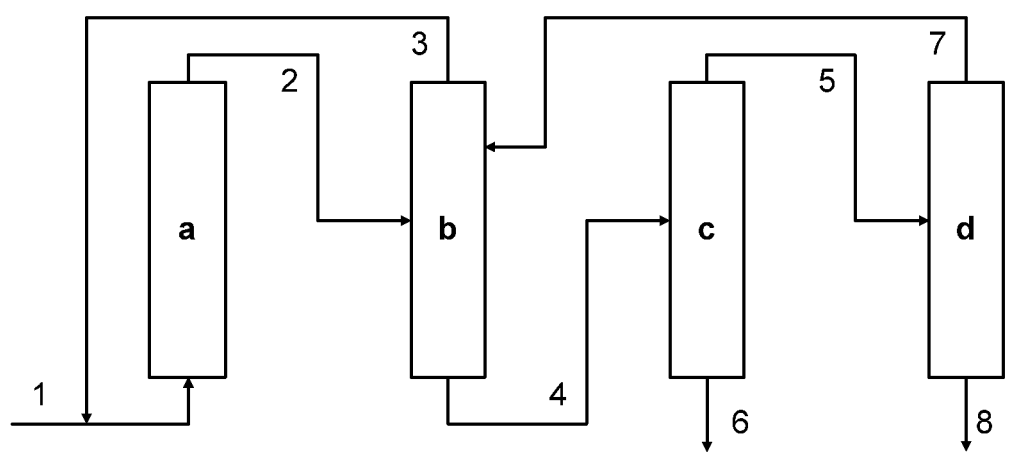

Removal of Methylamine and Ethylamine From a Product Mixture by Sequential Distillation FIG. 3 shows the separation of an ethylene amine synthesis mixture after performing the reaction in unit "a". The reaction in unit "a" is the same as in the Comparative Example. The product mixture, stream 2, is distilled at 23 bar and with a bottom temperature of 182° C. The top stream, stream 3, is re-circulated back to the reactor. The bottom stream, stream 4, is distilled in column "c" at 2.1 bar and with a bottom temperature of 156° C. The bottom stream, stream 6, consists of the desired ethylene amines and is distilled further to form the different amines produced. The top stream, stream 5, from column "c" is distilled further in column "d" at 23 bar and with a bottom temperature of 114° C. The top stream, stream 7, is re-circulated back to column "b", and the bottom stream, stream 8, consists of the undesired methylamine and ethylamine. The composition of the streams can be seen in Table 3.

TABLE 3

| Stream[1] | 2 | 3 | 4 | 5 | 6 | 7 | 8 |
|---|---|---|---|---|---|---|---|
| $NH_3$ | 46.3 | 99.9 | 4.9 | 93.1 | — | 99 | 1.4 |
| Amines[2] | 47 | — | 83 | — | 87.7 | — | 0.6 |
| Water | 6.5 | — | 11.8 | 0.4 | 12.3 | — | 5.8 |
| Methylamine | 0.09 | 0.07 | 0.15 | 2.8 | — | 1 | 31.5 |
| Ethylamine | 0.11 | 0 | 0.19 | 3.7 | — | — | 60.7 |

[1]expressed as a percentage
[2]produced ethyleneamines

Example 4

Removal of Methylamine from an Ammonia-Based Mixture by Adsorption Using 2-Methylphenol as Adsorbent A 1-litre glass round-bottom flask with a single opening was closed by a cap with a septum through which a sampling port was connected to a gas chromatographic (GC) analyzer. Prior to closing the flask the adsorbent used was weighed and poured into the vessel. After that the ammonia gas was flown in. Methylamine gas was injected through the septum with a special gas syringe. 5 ml of methylamine per litre of ammonia, at room temperature and a total pressure of 1 atm, was introduced in the vessel. 2-methylphenol (ex Merck) was used as received. It was in the form of fine dry particles.

After allowing 1 hour of contact, a sample of the gas from the headspace was taken for GC analysis. Prior to this test it was confirmed that the time of 1 hour is sufficient to reach equilibrium of the system.

The analysis was done on a Mega 8160 Fisons instrument, using a CP Volamine column of 60 m, with an internal diameter of 0.32 mm. Samples of 100 µl were injected into an injector at 250° C. The initial column temperature was 40° C., and it was increased up to 120° C. at a rate of 10° C./min. The carrier gas was helium and the used detector was FID at 250° C.

The concentration of the amine remaining in the gas phase at equilibrium was measured for different quantities of the introduced adsorbent. The results are given in the following Table 4.

TABLE 4

| 2-methylphenol introduced (g/$V^{feed}$) | Remaining amine relative to the initial value (%) |
|---|---|
| 3.65 | 11.5 |
| 6.89 | 5.3 |
| 3.55 | 1.4 |

The obtained results show adsorption of the amine, depending on the quantity of the adsorbent, and selectivity towards the amine relative to the ammonia, as the amine-to-ammonia ratio adsorbed is higher than the amine-to-ammonia ratio in the initial mixture (feed).

Example 5

Removal of Methylamine from an Ammonia-Based Mixture by Adsorption Using Activated Carbon (NORIT® ROX 0.8) as Adsorbent The same experimental set-up, procedure, analytical method, and quantities as described in Example 4 were used. Activated carbon NORIT® ROX 0.8 acid washed extruded activated carbon was used as received.

The concentration of the amine remaining in the gas phase at equilibrium was measured for different quantities of the introduced adsorbent. The results are given in the following Table 5.

TABLE 5

| Norit ROX 0.8 introduced (g/$V^{feed}$) | Remaining amine relative to the initial value (%) |
|---|---|
| 0.64 | 32.21 |
| 0.98 | 22.64 |
| 2.07 | 8.65 |
| 2.30 | 22.90 |
| 2.27 | 19.98 |
| 1.20 | 24.02 |
| 0.61 | 32.01 |
| 2.06 | 4.4 |

The obtained results show adsorption of the amine, depending on the quantity of the adsorbent, and selectivity towards the amine relative to the ammonia, as the amine-to-ammonia ratio adsorbed is higher than the amine-to-ammonia ratio in the initial mixture (feed).

Furthermore, the removal of amine in this case was somewhat better than in the case of 2-methyl phenol of Example 4.

Example 6

Removal of Methylamine from an Ammonia-Based Mixture by Adsorption Using Weakly Acid AMBERLITE® IRC76 as Adsorbent The same experimental setup, procedure, analytical method, and quantities as described in Example 4 were used. AMBERLITE® IRC76 weakly acidic cation exchange resin adsorbent, ex Rohm and Haas, was used in bead form.

The concentration of the amine remaining in the gas phase at equilibrium was measured for different quantities of the introduced adsorbent. The results are given in the following Table 6.

TABLE 6

| Amberlite IRC76 dry introduced (g/$V^{feed}$) | Remaining amine relative to the initial value (%) |
|---|---|
| 0.51 | 39.1 |
| 1.08 | 19.4 |
| 2.15 | 9.0 |
| 2.20 | 0.8 |

The obtained results show adsorption of the amine, depending on the quantity of the adsorbent, and selectivity towards the amine relative to the ammonia, as the amine-to-ammonia ratio adsorbed is higher than the amine-to-ammonia ratio in the initial mixture (feed).

Furthermore, the removal of amine in this case was slightly better than in the case of Norit Roxo in Example 5.

Example 7

Removal of Methylamine from an Ammonia-Based Mixture by Adsorption Using AMBERSORB® 563 as Adsorbent The same experimental set-up, procedure, analytical method, and quantities as described in Example 4 were used. AMBERSORB® 563 adsorbent (ex Rohm and Haas) was used as received.

The concentration of the amine remaining in the gas phase at equilibrium was measured for different quantities of the introduced adsorbent. The results are given in the following Table 7.

TABLE 7

| Ambersorb 563 introduced (g/$V^{feed}$) | Remaining amine relative to the initial value (%) |
|---|---|
| 0.48 | 25.5 |
| 2.06 | 4.4 |

The obtained results show adsorption of the amine, depending on the quantity of the adsorbent, and selectivity towards the amine relative to the ammonia, as the amine-to-ammonia ratio adsorbed is higher than the amine-to-ammonia ratio in the initial mixture (feed). Furthermore, the removal of amine in this case was comparable to that of Amberlite IRC76.

Example 8

Removal of Methylamine from an Ammonia-Based Mixture by Adsorption Using Strongly Acidic AMBERLYST® 15 as Adsorbent The same experimental setup, procedure, analytical method, and quantities as described in Example 4 were used. AMBERLYST® 15 strongly acidic ion exchange resin adsorbent, ex. Rohm and Haas was used in bead form, with surface area of 53 m$^2$/g and total pore volume of 0.40 cm$^3$/g.

The concentration of the amine remaining in the gas phase at equilibrium was measured for different quantities of the introduced adsorbent. The results are given in the following Table 8.

TABLE 8

| Amberlyst 15 Dry introduced (g/l$^{feed}$) | Remaining amine relative to the initial value (%) |
|---|---|
| 1.0 | 26.9 |
| 1.01 | 16.1 |
| 2.09 | 7.7 |
| 1.01 | 0.6 |
| 10 | 0.3 |

The obtained results show adsorption of the amine, depending on the quantity of the adsorbent, and selectivity towards the amine relative to the ammonia, as the amine-to-ammonia ratio adsorbed is higher than the amine-to-ammonia ratio in the initial mixture (feed).

Furthermore, the removal of amine in this case was even better than that with Amberlite and Ambersorb in Examples 6 and 7.

Example 9

Desorption of Adsorbed Methylamine from AMBERLITE® IRC76 by Washing with Ammonium Chloride Salt Solution Desorption of adsorbed methylamine from AMBERLITE® IRC76 weakly acidic cation exchange resin by washing with an aqueous ammonium chloride solution was evaluated. After applying the adsorption procedure as described in Example 4, adsorption resin was taken out and washed using 3M aqueous ammonium chloride solution.

Capillary zone electrophoresis was used as the analytical method to determine the concentration of the methylammonium ions in the aqueous ammonium chloride solution after desorption.

The quantity of desorbed methylamine relative to the adsorbed quantity shows full recovery of the adsorbed methylamine.

The invention claimed is:

1. Process to prepare ethylene amines by the amination of ethylene oxide, ethylene glycol or ethanolamine in the presence of a catalyst, comprising a step wherein methylamine and/or ethylamine are removed from the reaction effluents, wherein the aminating compound is ammonia.

2. The process of claim 1 wherein the excess of aminating compound is recycled for reuse in the process.

3. The process of claim 1 wherein after the amination reaction first excess aminating compound is removed together with the methylamine and/or ethylamine and subsequently the methylamine and ethylamine are removed from the aminating compound.

4. The process of claim 1 wherein after the amination reaction first the main part of the excess of aminating compound is removed and subsequently the rest of the excess aminating compound is removed together with the methylamine and/or ethylamine.

5. The process of claim 1 wherein methylamine and/or ethylamine are removed by a distillation step, an absorption step, an adsorption step, a cracking step or a combination of two or more of such steps.

6. The process of claim 5 wherein methylamine and/or ethylamine are removed by a distillation step.

7. The process of claim 2 wherein after the amination reaction first excess aminating compound is removed together with the methylamine and/or ethylamine and subsequently the methylamine and ethylamine are removed from the aminating compound.

8. The process of claim 2 wherein after the amination reaction first the main part of the excess of aminating compound is removed and subsequently the rest of the excess aminating compound is removed together with the methylamine and/or ethylamine.

9. The process of claim 2 wherein methylamine and/or ethylamine are removed by a distillation step, an absorption step, an adsorption step, a cracking step or a combination of two or more of such steps.

10. The process of claim 9 wherein methylamine and/or ethylamine are removed by a distillation step.

11. The process of claim 7 wherein methylamine and/or ethylamine are removed by a distillation step, an absorption step, an adsorption step, a cracking step or a combination of two or more of such steps.

12. The process of claim 11 wherein methylamine and/or ethylamine are removed by a distillation step.

13. The process of claim 8 wherein methylamine and/or ethylamine are removed by a distillation step, an absorption step, an adsorption step, a cracking step or a combination of two or more of such steps.

14. The process of claim 13 wherein methylamine and/or ethylamine are removed by a distillation step.

* * * * *